United States Patent [19]

Lesnick et al.

[11] 4,163,451

[45] Aug. 7, 1979

[54] INTERACTIVE METHOD AND DIGITALLY TIMED APPARATUS FOR CARDIAC PACING ARRHYTHMIA TREATMENT

[75] Inventors: Alan F. Lesnick; Peter P. Tarjan, both of Miami, Fla.

[73] Assignee: Cordis Corporation, Miami, Fla.

[21] Appl. No.: 845,650

[22] Filed: Oct. 26, 1977

[51] Int. Cl.² .............................................. A61N 1/36
[52] U.S. Cl. ........................................... 128/419 PG
[58] Field of Search ................... 128/419 PG, 419 PT

[56] References Cited

U.S. PATENT DOCUMENTS

| | | | |
|---|---|---|---|
| 3,921,642 | 11/1975 | Preston et al. | 128/419 PG |
| 3,942,534 | 3/1976 | Allen et al. | 128/419 PG |
| 4,005,282 | 1/1977 | Jennings | 128/2.1 R |

*Primary Examiner*—William E. Kamm

*Attorney, Agent, or Firm*—Kenway & Jenney

[57] ABSTRACT

The cardiac pacer disclosed herein responds to a premature heartbeat by first digitally measuring the time interval between a pair of successive sensed heartbeats and establishing an escape interval for stimulation which is shorter than the measured heartbeat interval. Pacing at this shorter escape interval enables the pacer to capture and control the heartbeat rate. By repeatedly incrementing the digital value representing the escape value on successive stimulated heartbeats, the heart is then caused to slow down until a preselected desired rate is established. Preferably, the sensing and timing between heartbeats continues during the slowdown process so that, if, at any time, a natural heartbeat occurs earlier than the stimulation pulse at the then extant escape interval, the escape interval is reset to a shorter time so that capture will be re-established.

15 Claims, 6 Drawing Figures

| DOWN COUNTER | | UP COUNTER | | | INTERVAL |
|---|---|---|---|---|---|
| BEGIN | END | BEGIN | END | PRESET | |
| 101 | — | 0 | 100 | 0 | 100 |
| 101 | — | 0 | 100 | 0 | 100 |
| 101 | 21 | 0 | 80 | 21 | 80 |
| 101 | 22 | 21 | 100 | 22 | 79 |
| 101 | 21 | 22 | 102 | 21 | 80 |
| 101 | 20 | 21 | 102 | 20 | 81 |
| 101 | 19 | 20 | 102 | 19 | 82 |
| 101 | 18 | 19 | 102 | 18 | 83 |
| ... | ... | ... | ... | ... | ... |

FIG. 2

| MEMORY ADDRESS | INSTRUCTIONS IN THE EIGHT CONSECUTIVE MEMORY LOCATIONS | | | | | | | |
|---|---|---|---|---|---|---|---|---|
| 0000 | 7100 | F800 | B8B9 | B4B1 | 3C08 | C4C4 | C4C4 | 3010; |
| 0010 | 1515 | 3927 | 87FC | 0135 | 31FC | 02E9 | F733 | 3317; |
| 0020 | 173D | 3915 | 1530 | 3DC4 | C4C4 | C4C4 | C4C4 | C430; |
| 0030 | 3D30 | 1B7A | C4C4 | 1530 | 3D17 | 1730 | 3DC4 | F816; |
| 0040 | FCFF | 3A40 | 69FA | 70F6 | F6F6 | F6FC | E6A8 | 69FA; |
| 0050 | 0FFC | F0A9 | F86D | A1F8 | 00A6 | 396A | 8715 | E070; |
| 0060 | 00FC | FF16 | 3A61 | 6A7A | 3000 | 0930 | 5E80 | FF67; |
| 0070 | 3397 | 1586 | E8F7 | 3B9B | F8E4 | A43F | 8336 | 9314; |
| 0080 | 1530 | 8814 | 1436 | 9114 | 86E4 | F7A7 | 7BF8 | 3DA0; |
| 0090 | D030 | 8815 | 1530 | 88F8 | 0EA0 | D0F8 | 05FC | FF3A; |
| 00A0 | 9D30 | 8D00 | 0000 | 0000 | 0000 | 0000 | 0000 | 0000; |
| 00B0 | 0000 | 0000 | 0000 | 0000 | 0000 | 0000 | 0000 | 0000; |
| 00C0 | 0000 | 0000 | 0000 | 0000 | 0000 | 0000 | 0000 | 0000; |
| 00D0 | 0000 | 0000 | 0000 | 0000 | 0000 | 0000 | 0000 | 0000; |
| 00E0 | 0000 | 0000 | 0305 | 0911 | 1A22 | 2A32 | 3A42 | 4A52; |
| 00F0 | A99A | 8D81 | 776F | 6760 | 5954 | 4E4A | 453E | 3731; |

INTERACTIVE METHOD AND DIGITALLY TIMED APPARATUS FOR CARDIAC PACING ARRHYTHMIA TREATMENT

BACKGROUND OF THE INVENTION

This invention relates to a method of cardiac pacing and apparatus for implementing the method and more particularly to a cardiac pacer for preventing and treating arrhythmias such as atrial tachycardia involving accelerated heartbeat rates. It is well known that premature heartbeats are a manifestation of the irritability of the heart. If untreated, the premature heartbeat may start long runs of rapid heartbeats.

Various systems have been proposed for treating arrhythmias involving increased heartbeat rates, e.g., atrial tachycardia, including the use of rate scanning as proposed in the Berkovits U.S. Pat. No. 3,698,398. The rate scanning program in these devices, however, is essentially predetermined rather than being interactive with the actual functioning of the heart. The rate scan proceeds on the assumption that capture will, at some point, be established and that the heart rate will track with the scanned rate down to the desired level. It is possible, however, that neither of these assumptions may be correct. Various other systems involving manual control have also been proposed but, as will be understood, these systems involve the availability and intervention of medically-cognizant personnel and such personnel will not be universally or instantaneously available, even in a hospital environment.

Among the several objects of the present invention may be noted the provision of cardiac pacing apparatus for treating or preventing arrhythmias involving accelerated heartbeat rates; the provision of such apparatus which is interactive with and responsive to the actual functioning of the patient's heart; the provision of such apparatus which effects capture by pacing the patient's heart using a timing which is adjusted in accordance with the last naturally occurring heartbeat; the provision of such an apparatus which is operative to re-establish capture if the natural heartbeat eludes pacemaker control during the slowdown operation; the provision of such apparatus which is highly reliable and which is of relatively simple and inexpensive construction. Other objects and features will be in part apparent and in part pointed out hereinafter.

SUMMARY OF THE INVENTION

Briefly, cardiac pacing apparatus in accordance with the present invention is based on digital timing techniques and involves timing means for generating a series of clock pulses, means responsive to heartbeats, and means for counting the clock pulses occurring from a first heartbeat to a second heartbeat thereby to obtain a first value representing the time interval between heartbeats. Further means, interconnected with the counting means, are provided for generating a digital value which is smaller than the first value by a preselected decrement and which represents an escape interval. Means are provided for counting clock pulses occurring after the second heartbeat, thereby to obtain a running time value and this running time value is compared with the escape interval value. When the running time value becomes substantially equal to the escape interval value, a stimulating pulse is generated and the escape interval value is increased by a preselected increment. Accordingly, the interval between successive stimulated heartbeats is gradually lengthened so as to slow down the patient's heart. In the preferred embodiments, the apparatus continues to be responsive to natural heartbeats and timing continues from the last heartbeat, natural or stimulated, and the escape interval is reset if a natural heartbeat occurs earlier than the then effective escape interval, thereby re-initiating the slowdown sequence.

BRIEF DESCRIPTION OF THE DRAWINGS

FIG. 2 is a table representing a sequence of values appearing in different registers in the embodiment of FIG. 1 during operation;

Corresponding reference characters indicate corresponding parts throughout the several views of the drawings.

DESCRIPTION OF THE PREFERRED EMBODIMENTS

Figure 1:
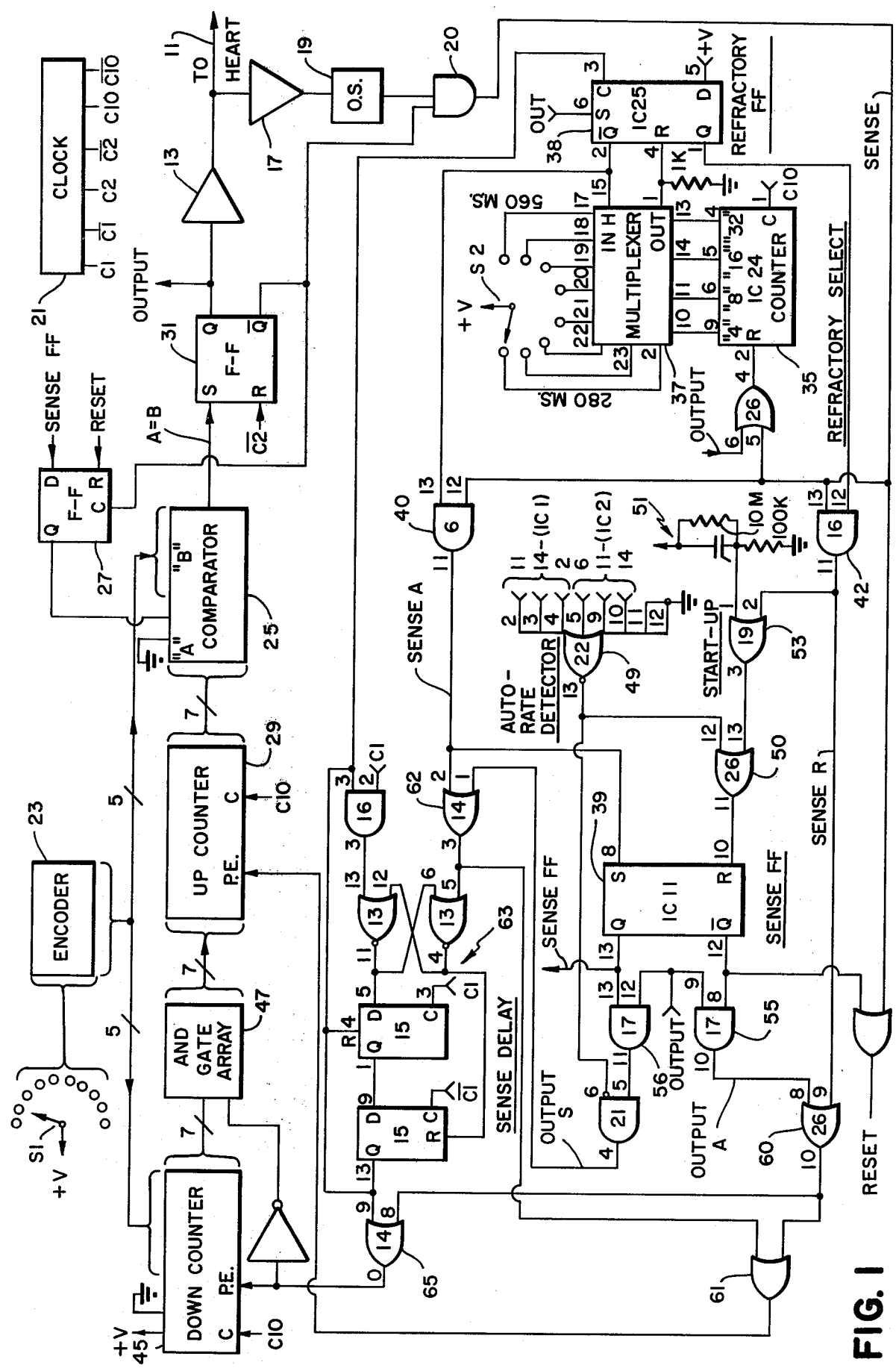
FIG. 1 is a block diagram of a cardiac pacer in accordance with the present invention, constructed using discrete components.

As indicated previously, the apparatus shown in FIG. 1 is a so-called hardwired version of the apparatus in accordance with the present invention. The apparatus was designed for bedside operation with controls for enabling the attending physician to preselect certain parameters by means of multi-position switches. With reference to FIG. 1, the physician may select, by means of a multi-position switch S1, the AUTO rate, i.e., the rate which the pacer will attempt to maintain. In other words, this value specifies the final rate toward which the pacer attempts to lead the heart.

The physician may likewise select, by means of a multi-position switch S2, a desired refractory period. As is understood by those skilled in the cardiac pacer art, cardiac pacing apparatus is typically provided with means defining an interval following a natural or stimulated heartbeat during which the apparatus is insensitive or refractory to further input signals.

As indicated previously, the apparatus of the present invention employs digital timing and for this purpose comprises an oscillator or other timing circuit appropriate for generating regular timing clock pulses at predetermined intervals. The embodiment shown in FIG. 1 employs a clock circuit 21 generating a first clock signal C1 having a period of one millisecond, a second clock signal C2 having a period of two milliseconds and a third clock signal C10 having a period of ten milliseconds. The complements of these signals, designated $\overline{C1}$, $\overline{C2}$ and $\overline{C10}$ are also provided. The basic counting and timing interval of the system is ten milliseconds but the one and two millisecond intervals are used for certain delay and output timing purposes, as explained hereinafter. The timing signals are employed at various points in the circuitry as indicated in the diagram of FIG. 1.

The pacer is provided with a unipolar or bipolar cardiac lead 11 which can be driven from a conventional pacer output stage or amplifier 13. The amplifier 13 is, in turn, controlled by a digital latch 31, an S-R type flip-flop. The latch 31 can be set, i.e., so as to initiate an output pulse, by a comparator 25 described hereinafter. Once set, the latch is reset by the $\overline{C2}$ clock signal to terminate the stimulation pulse. For this purpose, the lead 11 is also connected to a sense amplifier 17 and a one-shot multivibrator circuit 19. Multivibrator 19 provides a squared-up or digital type of signal which indicates the occurrence of a hearbeat. Sensed signals due to the pacer's own output signals are blocked and by an AND gate 20, the resultant signal being designated SENSE. While a single active lead is shown, it should be understood that separate input and output leads are also known in the art and it should be understood that such interfacing schemes may be employed in connection with the present invention also.

The AUTO rate select switch S1 is connected with an encoder circuit 23 which provides a binary encoded representation of the period corresponding to the selected final pacing rate. The units in which the selected period is represented are the ten millisecond timing intervals and only the higher level binary values are outputed from the encoder, i.e., the 4, 8, 16, 32 and 64 valued outputs. Thus, the smallest change in AUTO rate which can be selected is that corresponding to a change in period of 40 milliseconds. Even this, however, is much finer resolution than is required for most purposes.

The binary value representing the period corresponding to the selected AUTO rate is applied to the five higher bits of the seven-bit digital comparator circuit 25. The lowest level bit of this input is tied low, i.e., permanently given a binary value of "zero," while the second least significant bit is controlled by D-type flip-flop 27. This flip-flop may be considered to be the slow-down control flip-flop and its operation is described in greater detail hereinafter. The other binary input value provided to the comparator 25 is generated by a presettable up counter 29. Basically, this is the counter which times the interval between the last heartbeat and the next scheduled stimulating pulse, i.e., the escape interval. This counter is normally driven by the C10 clock pulse, as indicated.

In the absence of any arrhythymia involving an accelerated heartbeat rate, i.e., with the flip-flop 27 in its reset state, the up counter 29 is normally preset to an all zero state. Accordingly, after an interval corresponding to the preselected AUTO rate, the comparator 25 will provide an output signal indicating equality between the two binary inputs, this signal being indicated as A=B in the drawing. This output signal sets the output latch 31 which, in turn, drives the output amplifier 13. The output latch is reset by the next $\overline{C2}$ clock signal transition so that a stimulation pulse of one millisecond duration or width is generated. The output signal from the output latch, designated OUTPUT, is also employed at various points in the control circuitry, as indicated in the drawings, for purposes described in greater detail hereinafter. Assuming that no earlier natural hearbeat occurred, the generation of a stimulating pulse again effects a presetting of the up counter 29 in an all zero value so that the cycle is re-initiated. Thus, the pacer will continue to stimulate at the selected AUTO rate.

A counter 35 is interconnected with the refractory period selection switch 2 through a multiplexer 37 which serves to determine when the counter value reaches a level corresponding to the selected refractory period value. When the counter reaches this value, multiplexer 37 generates an output signal which will reset the D-type flip-flop 38. This flip-flop can be set by either a pacer output signal or by a sensed heartbeat signal which reaches this flip-flop through delay circuitry described hereinafter. In general, the function of the refractory flip-flop 38 is to steer the sense signal in dependence on whether the refractory period has passed or not. This steering is effected by a pair of AND gates 40 and 42 to obtain a SENSE A signal which indicates a heartbeat occurring after the refractory period, i.e. in the alert period, and a SENSE R signal which indicates a heartbeat occurring during the refractory period.

Timing between successive heartbeats, whether naturally occurring or stimulated, is accomplished essentially by a down counter 45, a related escape interval being established when the contents of the down counter are transferred, through a gate array 47 to the preset inputs of the up counter 29. However, before describing the operation of the down counter 45 it is useful to describe various control circuits which determine the sequence of operations of the down counter 45 and the transfer through gate array 47.

In order to determine when the system is in or has reached its AUTO rate, the six most significant output bits from the down counter 45 are applied to a NOR gate 49 which operates as an AUTO rate detector. Detector 49 provides an output signal when these bits are all zero. Among other functions, this signal operates, through OR gate 50, to reset a S-R flip-flop 39 which is conveniently designated the sense flip-flop. This flip-flop can also be set by a start-up pulse which is generated on the operation of a power-on start-up circuit comprising differentiator 51 and OR gate 53. The purpose of this circuitry is to establish the pacer at its selected AUTO rate when the system is first turned on. The sense flip-flop 39 may be set in response to the occurrence of a SENSE signal after the refractory period. The sense flip-flop controls gating circuitry, AND gates 55 and 56 which, in effect, steer the OUTPUT signal so as to obtain an OUTPUT A signal which indicates operation in the AUTO rate mode or an OUTPUT S signal which indicates operation in the progressive slowdown mode. These steered signals are utilized at other points in the control circuitry, as indicated in the drawing.

The presetting of the UP counter 29 to an all-zero state is effected by either the SENSE R or OUTPUT A signals, these signals being combined in an OR gate 60 and applied to the preset enable (PE) terminal of the counter 29 through an OR gate 61. The all-zero state is obtained since one of the inputs to each of the AND gates making up array 47 will be at a binary zero thus blocking the value then held in the DOWN counter 45. Loading of the UP counter 29 with the contents of the DOWN counter 45 is effected upon the occurrence of the SENSE A or OUTPUT S signals, these signals being combined in an OR gate 62 which then feeds the OR gate 61 mentioned previously. In order to permit the contents of the down counter 45 to be transferred to the up counter 29 in response to either an OUTPUT S pulse or a SENSE A pulse and then again immediately preset the down counter in response to these same signals, a sense delay circuit is provided, as indicated at 63, which can be triggered by either the OUTPUT S or SENSE A signals. This is a clocked or synchronous delay circuit which operates, in conjunction with the C1 timing signal and its complement $\overline{C1}$, to provide an output signal after a 1.5 millisecond delay. This signal is applied through an OR gate 65 to the preset enable input of down counter 45. The other input of the OR gate 65 is the Ored combination of the OUTPUT A signal with a SENSE R signal. The output from the OR gate 65 is also applied through an inverter 67, as the other input to each of the seven AND gates which controls the transfer of the seven bits of output information from down counter 45 to the preset inputs of up counter 29. In other words, when the output of gate 65 is high, the preset input of up counter 29 will see all zeros whether or not there is any residual value in the down counter 45.

In addition to controlling the transfer of values from the down counter to the up counter, the output signal from the delay circuit 63 is also applied to the clock input of the refractory flip-flop 38 to cause it to be set.

OPERATION

The operation of the FIG. 1 embodiment in controlling arrhythmias involving accelerated heartbeat rates is as follows. In this operational description, it is assumed: (1) that the AUTO rate select switch is set to a rate corresponding to a 1000 millisecond period, i.e., 1 heartbeat per second; (2) that the refractory select switch is set to 400 milliseconds; and (3) that the system has been started and is running at its AUTO rate. During running at the AUTO rate, each ouput signal, applied through the gate 65, will cause the down counter 45 to be preset to the value which is one unit higher than the binary value corresponding to the AUTO rate. The six most significant bits are determined directly from the AUTO rate encoder 23 while the least significant bit is tied high, as indicated in the drawing, and the next least significan bit is tied low. Accordingly, a preset value is provided which is one higher than the AUTO rate value. The up counter, however, will be preset to zero since the inverted input to the gate array 47 will cause all zeros to be presented to the preset inputs of the up counter. Following the OUTPUT pulse, the down counter will be stepped downward at each 10 millisecond interval. This counting, as suggested previously, provides a measurement of time passing since the last heartbeat. At the same time, the up counter is stepped up in value by the C10 10 millisecond clock signal and, as also suggested previously, this counting is, in effect, timing the then extant escape interval. If no natural heartbeat occurs before the end of the escape interval, a stimulation pulse will be generated when the comparator 25 indicates equality. The pacer will thus deliver a pulse at the period corresponding to the preselected AUTO rate and will repetitively so operate.

If, however, a naturally occurring heartbeat is sensed before the end of the then extant escape interval, i.e., during the alert period, the SENSE A signal will cause the up counter to preset while the gating array 47 is enabled. Thus, the up counter 29 will acquire the then extant value present in the down counter 45. One and one-half milliseconds thereafter, the down counter will be again preset to a value which is one greater than the value representing the AUTO rate. For the purposes of the following description, it will be assumed that a naturally occurring heartbeat was sensed 800 milliseconds, i.e., 80 counting intervals, after the last stimulating pulse delivered in the AUTO rate mode. The SENSE A signal will also set the sense flip-flop 39.

As will be understood, the presetting of the up counter 29 to the residual value in the down counter 45 in effect gives the up counter a headstart toward reaching the value with which it is being compared by comparator 25. Thus, the escape period is effectively shortened. Further, this headstart is based upon the interval measured by the down counter since the last heartbeat and is, in fact, one unit less than that interval. This follows since the down counter is stepped downwardly and its starting point is one greater than the binary value corresponding to the preselected heartbeat period. Accordingly, the new escape interval is also one timing interval shorter than the previous interval between heartbeats. For this particular example, the down counter would have decremented from 101 to 21 during the 80 counting intervals. This is indicated in the third line of the table of FIG. 2, the first two lines being illustrative of operation in the AUTO rate mode.

The shortened escape interval operates in the same manner as the present AUTO rate escape interval to cause the output circuitry to generate a stimulation pulse if no natural heartbeat occurs before the end of the escape interval. Thus, the apparatus has, in effect, digitally measured the heartbeat period and then set itself to deliver a stimulation pulse after a slightly shorter interval, a procedure likely to be effective in obtaining capture and control over the heart rate. Thus, following the naturally occurring heartbeat, the up counter will run for 79 counts, i.e., 790 milliseconds, before a stimulation pulse is generated. During this same interval, the down counter will have been stepped down 79 counts, i.e., from the initial preset value of 101 to a value of 22.

Since the down counter 45 did not, in the previous interval, reach a value such that the six most significant bits are all zeros, the AUTO rate detector 49 will not reset the sense flip-flop 39. Accordingly, the next output pulse will cause the slowdown flip-flop 27 to change state so that the "two" input of the input of comparator 25 is raised, i.e., a binary one is placed on this input. As will be understood by those skilled in the art, this will increase the value to which the up counter 29 must count by two increments before the comparator 25 determines equality.

Thus, although the next residual value to be transferred from the down counter 45 to the up counter 29 is one greater than the previous value, i.e., 22 rather than 21, the up counter itself must now count to a value which is higher than the preset AUTO rate by two, i.e., 102 rather than 100. Thus, the actual escape interval will be one timing unit longer than the first escape interval following the naturally occurring heartbeat. That is, the second escape interval will be 80 units or 800 milliseconds. At this point, the entire apparatus has transferred into the slowdown mode and the process of stretching out the escape interval continues. At the end of 80 counts, the down counter 45 will have been stepped down to a value of 21 and this value will be entered into the up counter. Accordingly, 81 counts will have to take place before the output pulse is generated. After these 81 time increments, the down counter will have reached a value of 20 and this value will have been transferred to the up counter leading to a new escape interval of 82 units, i.e., 820 milliseconds. This sequence is illustrated in the Table of FIG. 2 and, from the foregoing explanation and this Table, it will be seen that the escape interval will continue to lengthen, i.e., the stimulation rate will gradually slow down, so as to slow down the patient's heart. This assumes that capture is maintained. The slowing process continues until the escape interval corresponds to a present AUTO rate. At this point, the AUTO rate detector will cause the sense flip-flop 39 to revert to the AUTO rate condition and the entire circuit will revert to the initial mode of operation described previously.

The foregoing explanation assumes that the slowdown operation proceeds to completion. The device does, however, remain sensitive to earlier occurring natural heartbeats. If such should occur, the SENSE A signal thereby generated will cause the up counter 29 to acquire the then extant value present in the down counter 45. Since this value represents a measurement of the interval between the preceding two hearbeats, less one timing unit, it can be seen that the escape interval is again reset to a value just slightly shorter than the preceding heartbeat interval. Thus, the device attempts to again regain capture based on a timing or escape interval which is predicated on the interval between the preceding two heartbeats. In this manner, the chances of re-establishing capture are greatly improved as opposed to some empirically imposed sequence or program of stimulation.

If a heartbeat is sensed during the refractory period, the pacer reverts to its AUTO rate, this being deemed a safer expedient than ignoring the event.

Figure 3:
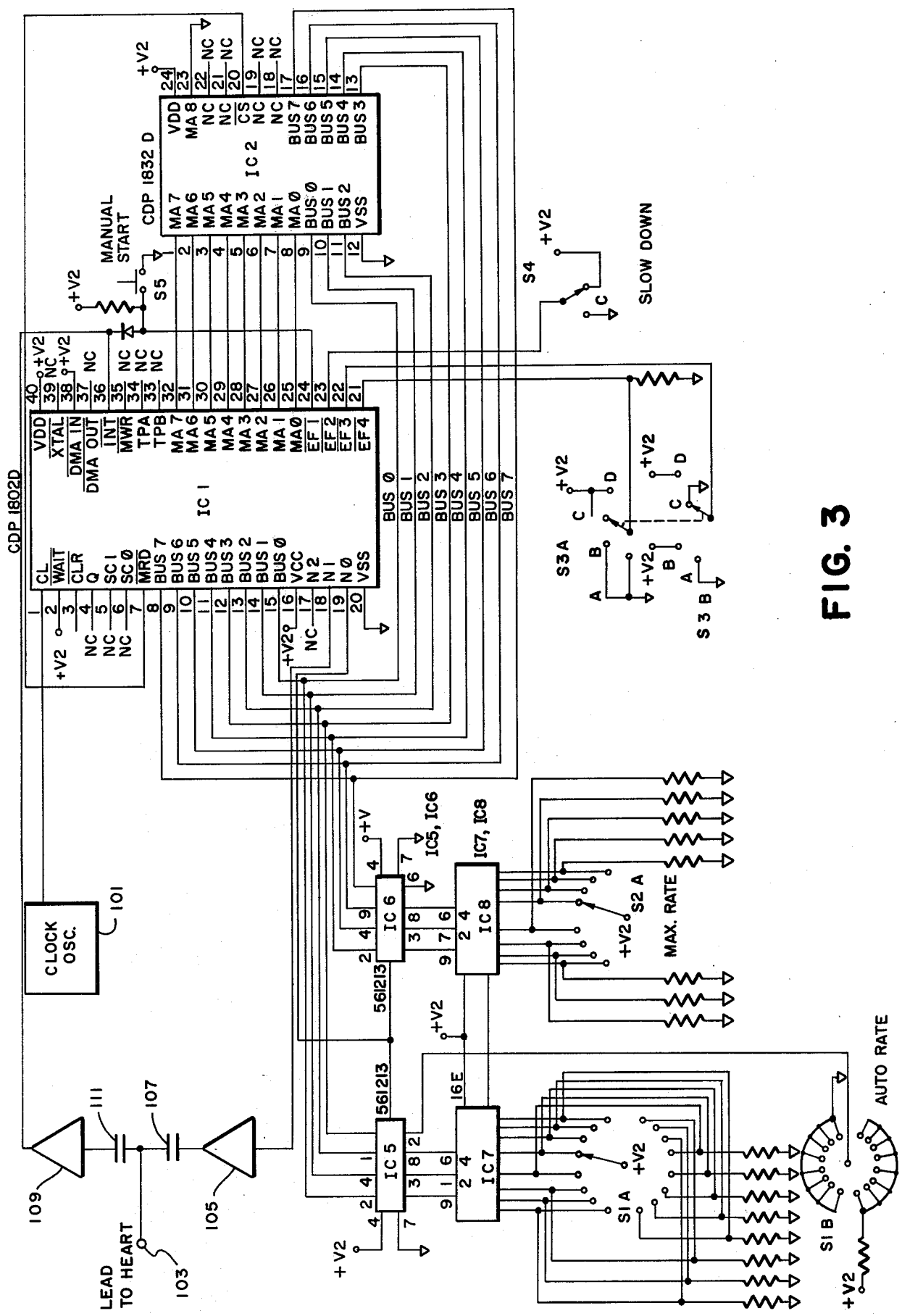
FIG. 3 is a schematic diagram of a pacer in accordance with the present invention employing a microprocessor.

The embodiment illustrated in FIG. 1 is designed to be implemented with discrete digital logic components and a prototype conforming to this design was built and successfully operated. However, given the number of counters to be implemented and the variety of control states, the overall function is one which is appropriately implemented utilizing microprocessor controller techniques, the timing, counting and interaction routines being defined by a program stored in a read-only memory (ROM). Such an implementation is illustrated in FIG. 3 where the digital controller portions of the circuitry are diagrammed in detail, including the integrated circuit component designations and the pin designations in conventional format. The digital integrated circuits are all types available from RCA (Radio Corporation of America) and are all of the so-called C-MOS type, i.e., they are constructed using complementary metal oxide semiconductor fabrication techniques. As is understood by those skilled in the art, C-MOS integrated circuits have exceptionally low power consumptions and are thus admirably suited for battery-operated systems such as the cardiac pacer of the present invention. As is understood, the use of isolated, battery power is considered essential for therapeutic systems, even where the pacing apparatus is not implanted.

The micropressor itself is model CDP-1802D, while the memory is a model CDP-1832D, appropriately programmed by mask during manufacture. The actual machine code program which is stored in the memory, is given in the Table of FIG. 5 where both the addresses and the instructions are stated in conventional hexadecimal format. This program is also given in an Appendix which is accompanying this Application upon filing. The Appendix statement of the program also includes the mnemonic instruction designation and the programmer notes which facilitate an understanding of the actual machine code implementation. It is expected, however, that this Appendix will be cancelled from the Application before allowance in that the detailed program implementation is not considered to be particularly useful in teaching the actual inventive concepts nor to constitute a matter suitable for a printed patent. It is believed sufficient that this material be publicly available in the prosecution file of the Application.

In that the number of intermediate values which must be dealt with at any given time are fairly limited, the internal registers of the CDP-1802D micropressor provide sufficient working storage and no separate random access memory (RAM) is needed. The memory address lines from the microprocessor are thus connected directly to the address terminals of the read-only memory. The CDP-1802D micropressor is a bus oriented machine and thus the data lines from the read-only memory are connected directly to the bus lines, as indicated in the drawing.

In this embodiment, sixteen possible rates are provided for operation in the AUTO rate mode and the operative rate is selected by means of a sixteen-position switch comprising two decks S1A and S1B. Integrated circuit 1C7, an RCA CD-4066, performs a one-of-eight to binary encoding function on the setting of the first switch deck S1A to provide the three least significant bits in a coded designation of the switch setting while the other switch deck S1B directly provides the most significant bit, as may be seen from the drawing. The resultant four bit code is applied through a quad bilateral switch circuit IC5 to four of the eight bus leads. These switches are enabled under the control of the N$\phi$ I/O command output of the microcomputer.

An eight position switch S2 is provided to designate a maximum rate for the operation of the pacer. In this embodiment, a maximum rate setting is used in place of the adjustable refractory period implemented in the embodiment of FIG. 1. The setting of switch S2 is encoded in a similar fashion by integrated circuit IC8 which is again a CD-4066 one-of-eight to binary encoder. This encoded data is provided to the next three of the bus leads, the remaining eighth bus lead being tied low (binary zero) during enablement of the bilateral switches IC5 and IC6. The bilateral switches IC5 and IC6 are also RCA integrated circuits, type CD-4532.

As explained hereinafter, the microprocessor periodically reads the settings of the switches S1 and S2 to determine the AUTO rate and maximum rate parameters for use in various timing loops in the operating program. It should be understood that the binary code which represents each possible setting of the switches does not correspond to a binary value directly representing the corresponding time period, as was the case in the embodiment of FIG. 1. Rather, the period or rate corresponding to each switch setting can be arbitrarily preselected in devising the program for the apparatus. In other words, after reading the binary value indicating a given switch setting, the program causes the microprocessor to look up the appropriate corresponding period or rate parameter from a table which is incorporated in the stored program. Thus, the values for the available rates may be chosen essentially arbitrarily based upon medical considerations and not in accordance with any particular binary or other mathematical distribution.

A four-position switch, comprising two decks S3A and S3B, is connected to directly provide a binary code indicating which of the four settings is selected, the code being applied to the I/O FLAG terminals EF3 and EF4 of the microprocessor. As will be apparent herinafter, the setting of this switch designates the amount by which the escape period is to be shortened, relative to the interval between the preceding pair of heartbeats, upon the occurrence of an early spontaneous heartbeat indicating an arrhythmia such as tachycardia. This adjustment represents an additional degree of flexibiltiy over the embodiment of FIG. 1 in which the amount of lead time utilized to obtain capture of the heartbeat rate was hard wired to be equal to the amount by which the escape period was lengthened for each cycle during the slowdown mode. In the program given, the four "jump ahead" time values are 10, 20, 40 and 80 milliseconds.

The amounts of the lengthening for each cycle in the slowdown mode can be selected from two different values. This is accomplished by means of a switch S4 which applies either a binary zero or a one to the EF2 terminal of the microprocessor. These states are assumed to call for a 10 millisecond or 20 millisecond slowdown increment respectively. Manual starting or initiation of this system is provided by means of a pushbutton switch S5 which can pull the EF1 terminal of the microprocessor low. Like the switches S1 and S2, the I/O FLAGS EF1–EF4 are periodically read by the microprocessor under programatic control and corresponding adjustments are made in the timing parameters of the program operation.

Th clock input terminal of the microprocessor is driven from an appropriate clock oscillator circuit 101. It is assumed that the clock oscillator frequency is 9.6 Kiloherz to establish the appropriate time scale for the various timing and delay loops.

A unipolar lead system is assumed in the FIG. 3 embodiment with a terminal 103 being provided for connection to a lead which will then extend to the patient's heart. As is understood by those skilled in the pacing art, the output signal is typically referenced to the positive supply voltage for the system, this reference potential being coupled to the patient's body through a suitable ground plate or other means. Stimulating pulses can be applied to terminal 103 by means of a conventional output amplifier 105 through a d.c. blocking capacitor 107. The output circuit 105 is driven or controlled from the N1 I/O command terminal of the microprocessor, the microprocessor being operative to both initiate and time the duration of the output pulse.

A conventional sense amplifier and squaring circuit 109 is connected to the same terminal 103, again through a d.c. blocking capacitor 111. As in the previous embodiment, the sense circuit 109 is designed to shape and square a detected cardiac signal to obtain a signal appropriate for digital interfacing. The resultant signal is negative going and is applied directly to the interrupt terminal INT of the microprocessor. thus, any time a heartbeat is sensed, the microprocessor is transferred to a routine to test its own state and to determine the appropriate action. The negative-going sensed signal is also applied, through an isolation diode D1, to the I/O FLAG terminal EF1. The diode prevents the manual initiation signal from being applied to the interrupt terminal.

Figures 5, 6:
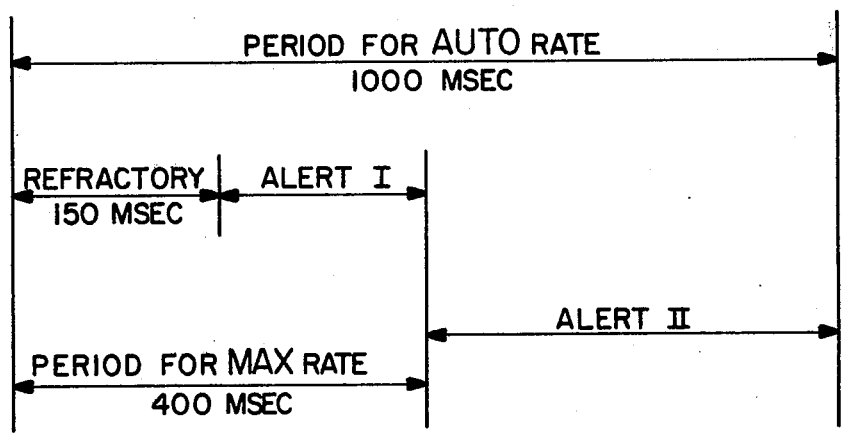
FIG. 5 is a representation of the program, in hexadecimal form.
FIG. 6 is a timing chart illustrating the phases of operation of the pacer of FIG. 3.

While the embodiment of FIG. 3 provides both a refractory period and a jump ahead/slow down mode of operation which are essentially the same as those provided by the FIG. 1 apparatus, there is also provided an intermediate mode in which a sensed pulse resets the timing circuitry but does not change the escape interval. This intermediate mode has been designated the ALERT I phase of the pacemaker operation as contrasted with the ALERT II phase which is like the jump ahead/slow down mode of operation of the FIG. 1 embodiment. The several portions of the timing cycle are illustrated in FIG. 6. As indicated, the overall period corresponds to the selected AUTO rate e.g., 1000 milliseconds. The refractory period is established by the program to be 150 milliseconds. The ALERT I phase exists from the end of the refractory period to the end of the period corresponding to the selected maximum rate, e.g., 400 milliseconds. The ALERT II phase, i.e., the portion of the timing cycle during which the pacer will perform its jump ahead/slow down operation, exists from the end of the ALERT I phase to the end of the period corresponding to the established AUTO rate. A third alert period can be introduced which is perhaps 50 ms long and starts 50 ms prior to the "auto rate" interval's end. During this time if a heartbeat is sensed, then the stimulator responds exactly as during ALERT I by inhibiting its output. In other words, the timing is reset but no stimulating pulse is generated.

Figure 4:
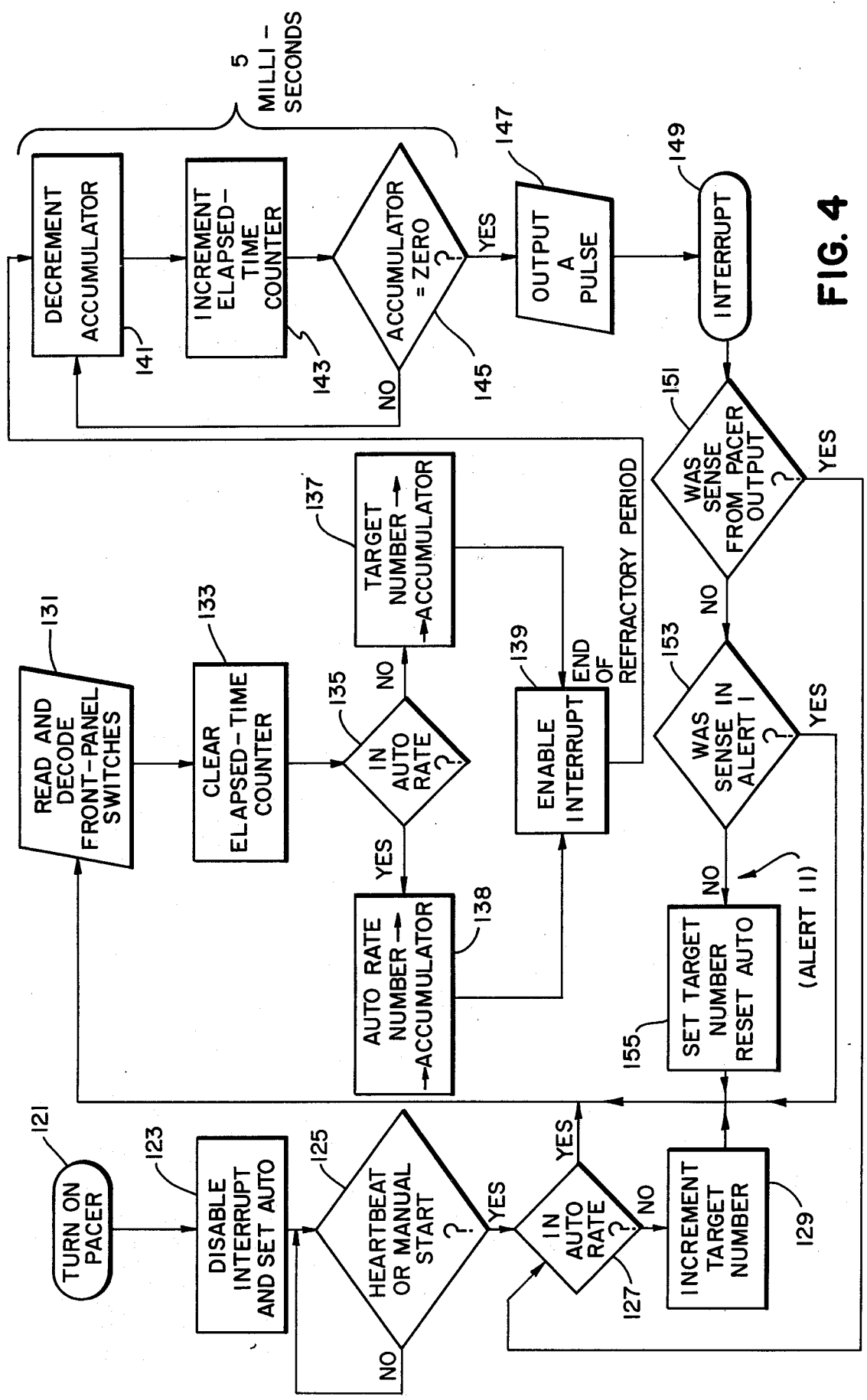
FIG. 4 is a flow chart for a stored program employed with the embodiment of FIG. 3.

An overall flow chart for the program which establishes this mode of operation is given in FIG. 4 and the best explanation of the operation of the FIG. 3 apparatus is believed to be referenced to this overall flow chart. When the pacer is initially turned on, as indicated at block 121 in the flow chart of FIG. 4, the program initially disables the interrupt capability of the microprocessor and places the pacer in its AUTO rate mode. In the particular program implementation disclosed, this is done by setting an internal microprocessor flip-flop. The state of this flip-flop can be read by the program internally within the microprocessor and thus, through a signal "Q" indicating the state of the flip-flop is brought out through pin 4 of the microprocessor, this pin is left unconnected. The program then proceeds to the test or decision block indicated at 125. This test or decision is based upon testing the condition of the flag terminal EF1. As indicated earlier, this flag terminal can be set by either a heartbeat or the manual pushbutton. Thus, when the pacer is initially turned on, it waits until either the heartbeat is sensed or the physician operates the pushbutton switch S5 to initiate operation in the AUTO rate mode. Once operation is initiated, and the decision block 127 determines that the pacer is in its AUTO rate mode, the program proceeds to read and decode the setting of the front panel switches, as indicated at block 131 in the flow chart, and to clear the elapsed time counter, as indicated at 133.

Assuming the pacer is in its AUTO rate mode, as is again tested at block 135, the AUTO rate number, i.e. the number defining the period of the selected AUTO rate, is entered into the microprocessor's accumulator. At this point, the program enables the interrupt capability of the microprocessor, as indicated at block 139, and then proceeds to enter a timing loop comprising blocks 141, 143, and 145. The time required to reach the completion of block 139 is 150 milliseconds and this constitutes the end of the refractory period. For reasons which will be explained hereinafter, there are two possible paths for reaching this point. The program, however, is devised so that the time required to reach this point is the same for both paths. This adjustment may, for example, be made by including NOP (no operation) instructions in the program.

During each pass through the timing loop, the accumulator is decremented, as indicated at 141, and the elapsed time counter is incremented, as indicated at 143. In this embodiment, the accumulator essentially provides the function of timing out the escape intervals while the elapsed time counter measures the interval since the last heartbeat, either natural or stimulated.

When the escape interval is reached so that the accumulator's contents equal zero, as tested at block 145 of the flow chart, the program leaves the timing loop and generates an output pulse as indicated at 147. This, of course, assumes that the system has been allowed to run out the escape interval and that no heartbeat has been sensed since the end of the refractory period.

The generation of an output pulse is allowed to trigger an interrupt, indicated at block 149, in the same manner as the sensed heartbeat. The program tests, as indicated at block 151, to determine whether the sensed interrupt was generated by the pacer itself. This is determined by examining the contents of the program counter. Assuming that the sensed interrupt was caused by the generation of the pacer output pulse, the program proceeds to block 127 still proceeding on the assumption that the pacer is in its AUTO rate mode. The program thus re-enters the sequence starting at block 131. This mode of operation will continue indefinitely until a naturally occurring heartbeat is sensed earlier than the period corresponding to the selected AUTO rate, though after the refractory period.

If, during one of its cycles of operation, the pacer senses such a natural heartbeat after the end of the refractory period, i.e. while the system is in the timing loop indicated at blocks 141, 143, and 145, an interrupt will be generated. Such an interrupt will be acted upon by the microprocessor since the interrupt capability was enabled at the end of the refractory period. Sensing of an interrupt causes the program to jump to the block indicated at 149. Upon then testing an indicated at 151, the program will determine that the sensed interrupt was not caused by a pacer output pulse. The program thus proceeds to determine whether the sensed interrupt was in the ALERT I phase, as indicated at block 153 of the flow chart. This test is made by examining the contents of the elapsed time counter.

If the contents of the elapsed time counter indicate that the interval passed was so short that the corresponding rate was faster than the selected maximum rate, the system does not leave the AUTO rate mode. Rather, the program re-enters at block 131 which causes the elapsed time counter to be reset but does not establish a different escape interval. This mode of operation is thus somewhat like the inhibit mode used in some so-called demand pacers where the timing interval is re-initiated upon sensing a naturally occurring heartbeat. The provision of such a mode has been deemed useful in that it avoids having the pacemaker try to jump ahead of or establish an inordinately fast rate based upon a single premature ventricular contraction or other isolated artifact.

On the other hand, if the naturally occurring heartbeat is sensed during the ALERT II period, the program proceeds to block 155 and causes a target number to be set which represents or establishes a new escape interval. This target number is obtained by reading the elapsed time counter and by subtracting from that value the amount of jump-ahead time selected by means of the switch S3. Thus, a target number is arrived at which corresponds to a period shorter than the period between the sensed heartbeat and preceding heartbeat. At the same time, the program takes the pacer out of its AUTO rate mode. Accordingly, in proceeding from block 155, through blocks 131 and 133, the program will, upon reaching the decision block 135, proceed on the right hand path. Thus, as indicated at block 137, the accumulator will be loaded with the target number representing the then extant escape interval, rather than the AUTO rate number. Accordingly, after entering the timing loop, the amount of time required until an output pulse is generated will be based upon the target number and will thus be shorter than the preceding interval between heartbeats. This then is the jump-ahead portion of the pacer's operation. It may be noted that, if a spontaneous heartbeat is detected at the very beginning of the ALERT II period, the jump-ahead mode of operation may cause the escape interval to be momentarily shorter than the interval corresponding to the preselected MAX rate.

When an output pulse is then again generated, the sensed interrupt will be determined, at block 151, to be caused by the pacer itself so that the program will then move to the decision block indicated at 127. Here, however, it will be determined that the pacer is not in its AUTO rate mode and thus the program will proceed to block 129 where the target number is incremented. The amount of increment added to the target number at this point is that determined by the setting of the switch S4. This then establishes a larger target number, i.e. one corresponding to a longer escape interval. Accordingly, as the program proceeds through blocks 131, 133, and 135 to block 137, this new target number wll be entered into the accumulator and will then be used by the timing loop to cause an output pulse to be generated after this slightly longer interval. This then is the slowdown portion of the pacer's operation and this mode will continue to progressively lengthen the interval between stimulating pulses since the program path will continue to pass through the block 129 on each cycle of operation. This slowing down will continue until the test indicated at block 127 determines that the target number has reached a value equivalent to the AUTO rate number, at which point the system operation will then be returned to the AUTO rate mode and will continue to effect stimulation at that rate, as described previously.

It should be understood, however, that while the pacer is in its slowdown mode of operation, the system remains sensitive to naturally occurring heartbeats which may occur within that portion of the cycle after the end of the refractory period, any such signal being effective to generate an interrupt. If the naturally occurring heartbeat occurs during the ALERT I phase of operation, the timing operation will be merely reset but the same target number will be retained so that the slowing down will proceed from that point. If, however, the sensed naturally occurring heartbeat occurs during the ALERT II phase of operation, a new target number will be established based on the elapsed time between the last stimulating pulse and the naturally occurring heartbeat. The pacer will jump ahead of that interval, attempting to gain capture, and will then progressively slow down, again attempting to lead the heart to the selected AUTO rate.

While the presently preferred version of the microprocessor pacer includes a few features which are not found in the FIG. 1 embodiment, it should be understood that these features are not essential to the basic operation of the system and that they could be omitted so that the two embodiments would be identical in operation and external appearance. Likewise, the FIG. 1 discrete component embodiment could be modified to include the features which are now provided by the microprocessor-based version. It should thus be understood that both versions are thus embodiments of the same inventive concepts.

In view of the foregoing, it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. Cardiac pacing apparatus comprising:
    timing means for generating a series of clock pulses;
    means responsive to heartbeats;
    means for counting clock pulses occurring from a first heartbeat to a second heartbeat thereby to obtain a first value representing the time interval between heartbeats;
    means for generating a value which is smaller than said first value and which represents an escape interval;
    means for counting clock pulses occurring after said second sensed heartbeat to obtain a running time value;
    means for comparing said running time value with said escape interval value; and
    means responsive to said comparison for generating a stimulating pulse and for incrementing said escape interval value if said running time value becomes substantially equal to said escape interval value.

2. Cardiac pacing apparatus comprising:
    means for generating a series of clock pulses;
    means for counting, after a heartbeat, to obtain a time value based on said clock pulses;
    means for sensing heartbeats;
    means for preselecting an AUTO rate value representing a maximum interval between heartbeats;
    pulse output means, said pulse output means being operative to generate a stimulation pulse when said time value reaches a level corresponding to said AUTO rate value;
    means responsive to a sensed, naturally occurring heartbeat for generating an escape interval value which corresponds to a period shorter than the interval from the preceding heartbeat, said pulse output means being thereafter operative to generate a stimulation pulse when said time value reaches a level corresponding to said escape interval value; and
    means for incrementing said escape interval value each time a stimulation pulse is generated at the time corresponding to the then extant escape interval value.

3. Cardiac pacing apparatus comprising:
    means for generating a series of clock pulses;
    means for counting, after a heartbeat, to obtain a time value based on said clock pulses;
    register means for holding a value representing an escape interval;
    pulse output means, said pulse output means being operative to generate a stimulation pulse when said time value reaches said escape interval value;
    means for sensing heartbeats;
    means for preselecting an AUTO rate value representing a maximum interval between heartbeats and, in the absence of sensed naturally occurring heartbeats, entering said AUTO rate value in said register;
    means responsive to a sensed, naturally occurring heartbeat for generating an escape interval value which corresponds to a period shorter than the interval from the preceding heartbeat, and for entering said shorter value in said register; and
    means for incrementing said escape interval value in said register each time a stimulation pulse is generated until said escape interval value reaches said AUTO rate value.

4. Apparatus as set forth in claim 3 including means for preselecting the magnitude of the increments.

5. Apparatus as set forth in claim 3 including means for selecting the amount by which the initial escape interval is shorter than the interval between the sensed, naturally occurring heartbeat and the preceding heartbeat.

6. Apparatus as set forth in claim 3 wherein said means for counting comprises a discrete digital counter.

7. Apparatus as set forth in claim 6 wherein said pulse output means includes a discrete comparator.

8. Apparatus as set forth in claim 7 wherein said means for generating an escape interval value includes a second discrete digital counter and wherein said entering means includes means for transferring a value from said second counter to the first said counter.

9. Apparatus as set forth in claim 3 wherein said pulse output means includes means for comparing said time value with said escape interval value.

10. Apparatus as set forth in claim 9 wherein said means for counting and said means for comparing comprise storage registers and the accumulator of a microprocessor.

11. Apparatus as set forth in claim 10 wherein said sensing means generates an interrupt to said microprocessor.

12. Apparatus as set forth in claim 11 wherein the sequence of operations of said microprocessor is controlled by a program stored in a read only memory.

13. The method of electrically pacing a heart which comprises:
    sensing heartbeats;
    digitally timing the interval between successive heartbeats;
    generating an escape interval value which corresponds to a period shorter than the timed interval between a first heartbeat and a second, naturally occurring heartbeat;
    following a naturally occurring heartbeat, generating a stimulating pulse when the timed interval corresponds to the escape interval value and then incrementing the escape interval value, the incrementing continuing on successive stimulation cycles until said escape interval value reaches a preselected value corresponding to a minimum heartbeat rate.

14. The method of electrically pacing a heart which comprises:
    generating stimulating pulses at preselected intervals to effect pacing at a preselected fixed rate, the intervals being determined by digitally counting down a clock signal by a preselectable factor;
    sensing for naturally occurring heartbeats occurring during a period preceding the completion of each such preselected interval and, if a naturally occurring heartbeat is detected during said period, generating an escape interval value which corresponds to a period shorter than that between the sensed heartbeat and the preceding stimulated heartbeat;

following a detected, naturally occurring heartbeat, generating stimulating pulses at intervals corresponding to the then extant escape interval value by digitally counting down from said clock signal and, upon the generation of each pulse, incrementing the escape interval value, the incrementing continuing until the escape interval becomes essentially equal to said preselected interval at which point the pacing reverts to fixed rate.

15. Cardiac pacing apparatus for treating cardiac arrhythmias, said apparatus comprising:

pacer input means for electrically detecting heartbeats;

pacer output means for generating electrical signals at levels appropriate for cardiac stimulation;

means for coupling said input means and said output means to a patient's heart;

a digital data processor whose sequence of operation is controllable by means of a stored program, said processor including means for testing input parameters and means for generating output signals, said pacer output means being connected to said processor output signal generating processor to provide a changed input parameter thereto when a heartbeat is detected;

a read only memory having a program permanently stored therein, said program defining the sequential reaction of the processor output signal of input parameters coupled to said processor as a result of detected naturally occurring heartbeat sequences, said program including instruction sequences for measuring the intervals between successive heartbeats and revising stimulation sequences in response to the values obtained.

* * * * *